(12) United States Patent
Kamal et al.

(10) Patent No.: US 7,056,913 B2
(45) Date of Patent: Jun. 6, 2006

(54) C8—LINKED PYRROLO[2,1-C][1,4]BENZODIAZEPINE-ACRIDONE/ACRIDINE HYBRIDS

(75) Inventors: Ahmed Kamal, Hyderabad (IN);
Srinivas Olepu, Hyderabad (IN);
Ramulu Poddutoori, Hyderabad (IN);
Ramesh Gujjar, Hyderabad (IN);
Praveen Kumar Pogula, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 28 days.

(21) Appl. No.: 10/812,841

(22) Filed: Mar. 30, 2004

(65) Prior Publication Data

US 2005/0222132 A1 Oct. 6, 2005

(51) Int. Cl.
*C07D 401/12* (2006.01)
*A61K 31/4375* (2006.01)
*A61P 35/00* (2006.01)

(52) U.S. Cl. ..................... 514/220; 540/496
(58) Field of Classification Search ................ 540/496; 514/220
See application file for complete search history.

(56) References Cited

FOREIGN PATENT DOCUMENTS

| EP | 0 098 098 | 1/1984 |
|---|---|---|
| WO | 00 12508 | 3/2000 |

OTHER PUBLICATIONS

Kamal et al., Ahmed "Design, Synthesis, and Evaluation of New Noncross-Linking Pyrrolobenzodiazepine Dimers with Efficient DNA Binding Ability and Potent Antitumor Activity." J. Med. Chem.. (2002), 45, pp 4679-4688.

Thurston et al., David E. "Synthesis of Sequence-Selective C8-Linked Pyrrolo[2,1-c][1,4]benzodiazepine DNA Interstrand Cross-Linking Agents." J. Org. Chem. (1996), 61, pp. 8141-8147.

Schofield et al., Philip C. "Metabolism of N-[2-(dimethylamino)ethyl]acridine-4-carboxamide in cancer patients undergoing a phase I clinical trial." Cancer Chemother Pharmacol (1999), 44, 51-58.

Gamage et al., Swarna A. "A New Synthesis of Substituted Acridine-4-carboxylic Acids and the Anticancer Drug N-[2-(Dimethylamino)ethyl]acridine-4-carboxamide (DACA)." Tetrahedron Letters, (1997), 38, 4, pp. 699-702.

Thurston et al., David E. "Synthesis of DNA-Interactive Pyrrolo[2, 1-c][1,4]benzodiazepines." Chem. Rev. (1994), 94, pp. 433-465.

*Primary Examiner*—Bruck Kifle
(74) *Attorney, Agent, or Firm*—Ladas and Parry LLP

(57) ABSTRACT

The present invention provides novel pyrrolo-[2,1-c][1,4] benzodiazepine hybrids useful as anti-tumour agents and a process for the preparation thereof.

18 Claims, 1 Drawing Sheet

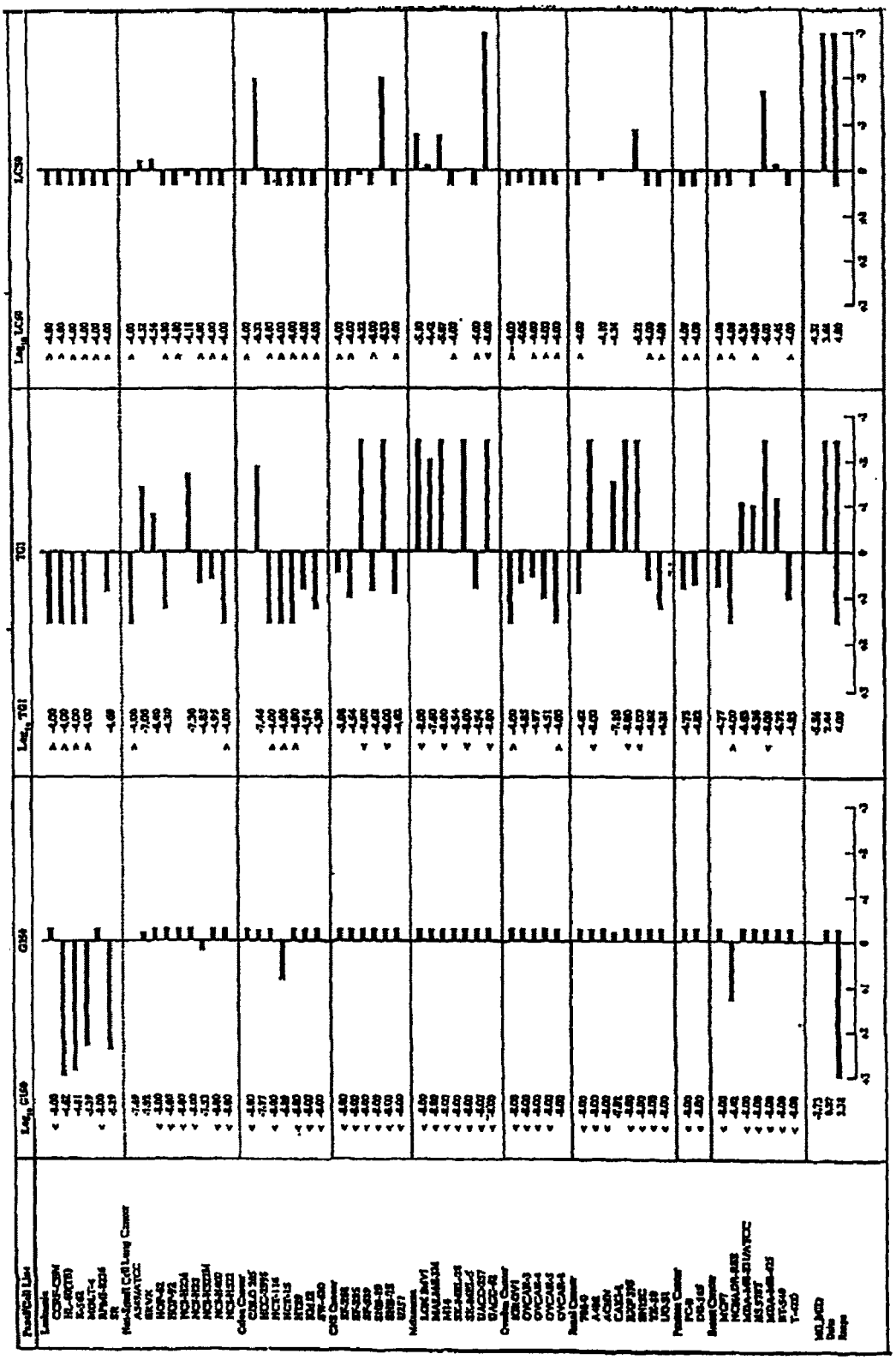

C8—LINKED PYRROLO[2,1-C][1,4]BENZODIAZEPINE-ACRIDONE/ACRIDINE HYBRIDS

FIELD OF THE INVENTION

The present invention provides novel pyrrolo-[2,1-c][1,4]benzodiazepine hybrids useful as anti-tumour agents. The present invention also provides a process for the preparation of new pyrrolo[2,1-c][1,4]benzodiazepine hybrids as antitumour agents. More particularly, the present invention provides a process for the preparation of 7-methoxy-8-[n'-(4"-acridonylcarboxyamido)alkyl]-oxy-(11aS)-1,2,3,11a-tetraydro-5H-pyrrolo[2,1-c][1,4]benzodiazepin-5-one and 7-methoxy-8-[n'-(4"-acridinylcarboxyamido)-alkyl]-oxo-(11aS)-1,2,3,11a-tetrahydro-5H-pyrrolo[2,1-c][1,4]benzodiazepin-5-one with aliphatic chain length variation of these compounds and it also describes the DNA binding, anticancer (antitumour) activity. The structural formula of the novel pyrrolo[2,1-c]-[1,4]benzodiazepines of the invention is given below:

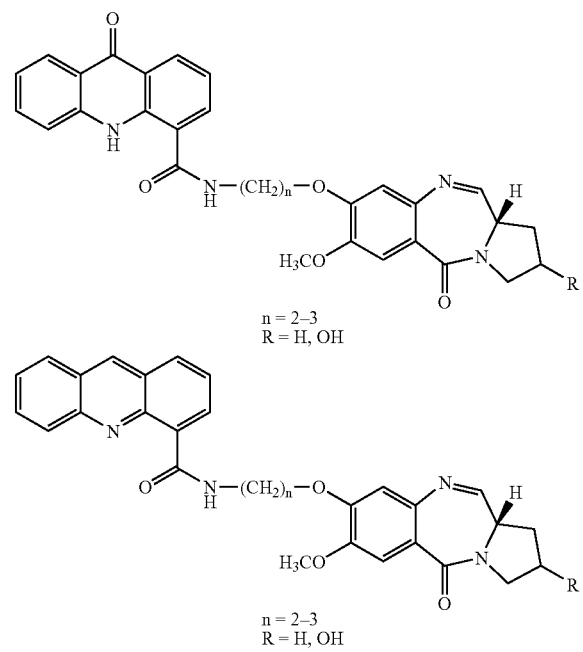

n = 2–3
R = H, OH n = 2–3
R = H, OH

BACKGROUND OF THE INVENTION

Pyrrolo[2,1-c][1,4]benzodiazepine antitumour antibiotics are commonly known as anthramycin class of compounds. In the last few years, a growing interest has been shown in the development of new pyrrolo[2,1-c][1,4]benzodiazepines (PBDs). These antibiotics react covalently with DNA to form an N2-guanine adduct that lies within the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; and Unezawa, H. *J. Antibiot.*, 1980, 33, 665.; Kohn, K. W. and Speous, C. L. *J. Mol. Biol.*, 1970, 51, 551.; Hurley, L. H., Gairpla, C. and Zmijewski, M. *Biochem. Biophys. Acta*, 1977, 475, 521.; Kaplan, D. J. and Hurley, L. H. *Biochmestry*, 1981, 20, 7572). The molecules have a right-handed twist, which allows them to follow the curvature of the minor groove of B-form double-stranded DNA spanning three base pairs. A recent development has been the linking of two PBD units through their C-8 positions to give bisfunctional alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S. and Hurley, L. H. *J. Org. Chem.*, 1996, 61, 8141).

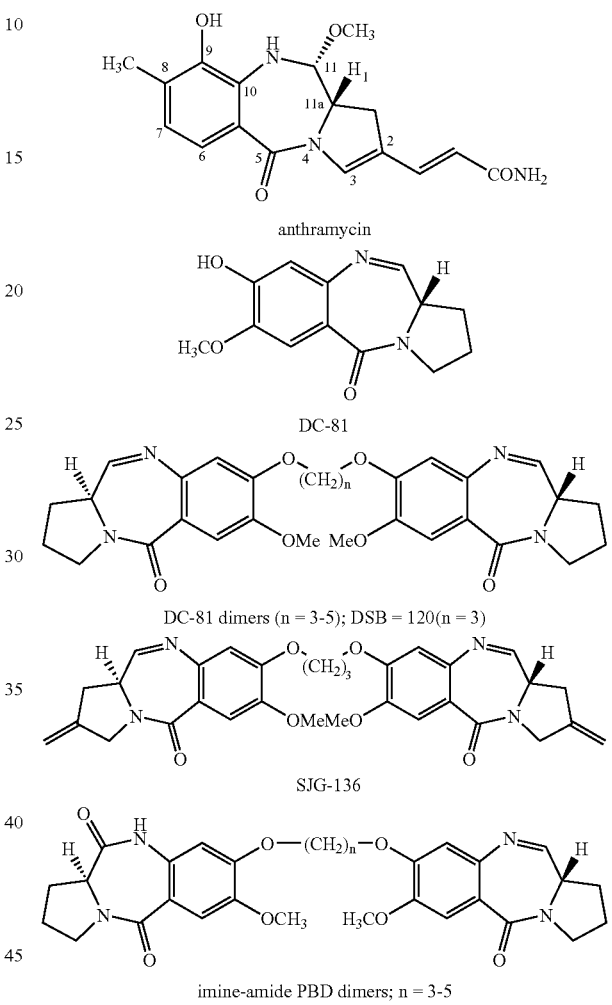

Recently, PBD dimers have been developed that comprises two C2-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. *J. Med. Chem.* 2001, 44, 737). Recently, a noncross-linking mixed imine-amide PBD dimers have been synthesized that have significant DNA binding ability and potent antitumour activity. (Kamal, A.; Ramesh, G.; Laxman, N.; Ramulu, P.; Srinivas, O.; Neelima, K.; Kondapi, A. K.; Srimu, V. B.; Nagarajaram, H. M. *J. Med. Chem.* 2002, 45, 4679).

Naturally occurring pyrrolo[2,1-c][1,4]benzodiazepines belong to a group of antitumour antibiotics derived from *Streptomyces* species. Recently, there is much impetus for the PBD systems as they can recognize and bind to specific sequence of DNA. Examples of naturally occurring PBD's include anthramycin, DC-81, tomaymycin, sibiromycin and neothramycin.

However, the clinical efficacy for these antibiotics is hindered by several limitations, such as poor water solubility, carbiotoxicity, development of drug resistance and metabolic inactivation.

OBJECTS OF THE INVENTION

The main object of the present invention is to provide new pyrrolo[2,1-c][1,4]-benzodiazepine hybrids useful as antitumour agents.

Another objective of the present invention is to provide a process for the preparation of novel pyrrolo[2,1-c][1,4]-benzodiazepine hybrids useful as antitumour agents.

SUMMARY OF THE INVENTION

Accordingly the present invention provides novel pyrrolo [2,1-c][1,4]benzodiazepine hybrids of formula IV or VII wherein R=H, OH and n is 2–3.

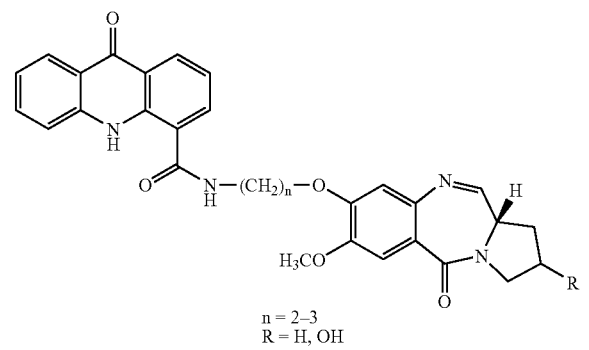

Formula IV n = 2–3
R = H, OH

Formula VII n = 2–3
R = H, OH

In one embodiment of the invention, the compound of the invention is selected from the group consisting of 7-Methoxy-8-[2'-(4"-acridonylcarboxamido)ethyl]-oxy-(11aS)1,2,3,11a-tetra-hydro-5H-pyrrolo[2,1-c][1,4]benzodiazepin-5-one; 7-Methoxy-8-[2'-(4"-acridonylcarboxamido)ethyl]-oxy-(4R)-hydroxy-(11aS)1,2,3,11a-tetrahydro- 5H-pyrrolo[2,1-c][1,4]-benzodiazepin-5-one; 7-Methoxy-8-[3'-(4"-acridonylcarboxamido)pyropyl]-oxy-(11aS)1,2,3,11a-tetrahydro-5H-pyrrolo[2,1-c][1,4]benzodiazepin-5-one; 7-Methoxy-8-[3'-(4"-acridonylcarboxamido)pyropyl]-oxy-(4R)-hydroxy-(11aS)1,2-3,11a tetrahydro-5H-pyrrolo[2,1-c][1,4]benzodiazepin-5-one, 7-Methoxy-8-[2'-(4"-acridinylcarboxamido)ethyl]-oxy-(11aS)1,2,3,11a-tetrahydro-5H-pyrrolo[2,1-c][1,4]benzodiazepin-5-one; 7-Methoxy-8-[2'-(4"-acridinylcarboxyamido)ethyl]-oxy-(4R)-hydroxy-(11aS)-1,2,3,-11a-tetrahydro-5H-pyrrolo[2,1-c][1,4]benzodiazepin-5-one; 7-methoxy-8-[3'-(4"-acridinylcarboxamido)propyl]-oxo-(11aS)1,2,3,11a-tetrahydro-5H-pyrrolo[2,1-c][1,4]benzodiazepin-5-one and 7-Methoxy-8-[3'-(4"-acridinylcarboxamido) propyl]-oxy-(4R)-hydroxy-(11aS)1,2,-3,11a tetrahydro-5H-pyrrolo[2,1-c][1,4]benzodiazepin-5-one.

The present invention also provides a process for preparation of pyrrolo-[2,1-c][1,4]benzodiazepine hybrids of formula IV and VII wherein R=H, OH and n is 2–3, Formula IV 15
n = 2–3
R = H, OH Formula VII

25 the process comprising reacting an acridone or an acridine acid with (2S)-N-[4-(n'-aminoalkyloxy)-5-methoxy-2-nitrobenzoyl]-pyrrolidine-2-carboxaldehyde diethyl thioacetal of formula I Formula I in the presence of EDCI and HOBt in organic solvent for a period of 24 h to obtain (2S)-N-{4-[n'-(4"-acrido-nylcarboxamido)-alkyl]-oxy-5-methoxy-2-nitrobenzoyl}pyrrolidine-2-carboxaldehyde diethyl thioacetal II/(2S)-N-{4-[n'-(4"-acridinylcarboxamido)-alkyl]-oxy-5-methoxy-2-nitrobenzyl}pyrrolidine-2-carboxaldehyde diethyl thioacetal of formula V where 'n' is 2–3,

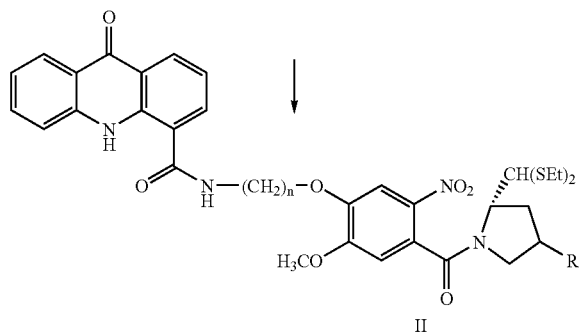

Formula II

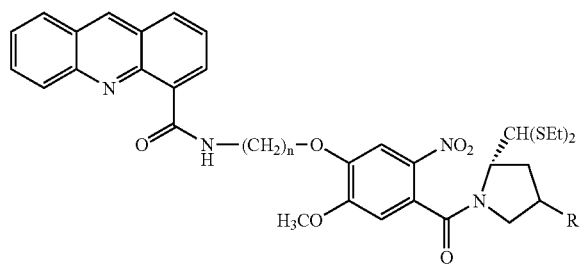

Formula V isolating the compound of formula II/formula V and then reducing the compounds of formula II/formula V with $SnCl_2 \cdot 2H_2O$ in presence of an organic solvent up to a reflux temperature, isolating the (2S)-N-{4-[n'-(4"-acridonylcarboxamido)-alkyl]-oxy-5-methoxy-2-aminobenzoyl}pyrrolid-dine-2-carboxaldehydediethylthioacetal of formula III/(2S)-N-{4-[n'-(4"-acridinylcarboxamido)-alkyl]-oxy-5-methoxy-2-aminobenzoyl}pyrrolidine-2-carboxaldehyde diethyl thioacetal of formula VI where n is 2–3 by known methods,

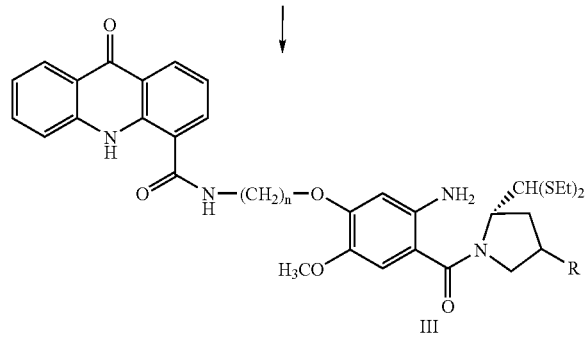

Formula III

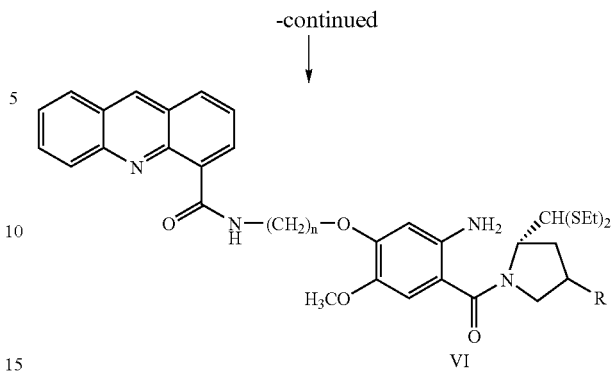

Formula VI reacting compound of formula III/formula VI with a known deprotecting agents in a conventional manner to give novel pyrrolo[2,1-c][1,4]benzodiazepine hybrids of formula IV/formula VII wherein n and R are as stated above.

In one embodiment of the invention, the organic solvent used for the reaction of the acridone/acridine acid with compound of formula I comprises dimethyl furan.

In another embodiment of the invention, the compound of formula II/formula V is isolated by washing with saturated $NaHCO_3$, brine, drying and evaporation of the solvent.

In another embodiment of the invention the organic solvent used during the reduction of compound of formula II/formula V comprises methanol.

In a further embodiment of the invention, the compound of formula III/formula V is isolated by adjusting the pH of the reaction mixture to about pH 8 with a saturated $NaHCO_3$ solution, diluting with ethyl acetate, filtering through celite and extracted an organic phase and drying the organic phase over $Na_2SO_4$.

In another embodiment of the invention, the deprotecting agent used for obtaining the compound of formula IV/formula VII comprises $HgCl_2$ and $CaCO_3$ in MeCN-water (4:1).

DETAILED DESCRIPTION OF THE INVENTION

The present invention provides novel pyrrolo[2,1-c][1,4] benzodiazepine hybrids of formula IV or VII wherein R=H, OH and n is 2–3 and also provides a process for the preparation thereof.

The process of the invention comprises reacting an acridone or an acridine acid with (2S)-N-[4-(n'-aminoalkyloxy)-5-methoxy-2-nitrobenzoyl]-pyrrolidine-2-carboxaldehyde diethyl thioacetal of formula I

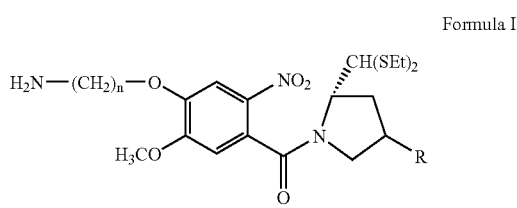

Formula I in the presence of EDCI and HOBt in organic solvent for a period of 24 h to obtain (2S)-N-{4-[n'-(4"-acrido-nylcarboxyamido)-alkyl]-oxy-5-methoxy-2-nitrobenzoyl}pyrrolidine-2-carboxaldehyde diethyl thioacetal II/(2S)-N-{4-[n'-(4"-acridinylcarboxamido)-alkyl]-oxy-5-methoxy-2-nitrobenzoyl}pyrrolidine-2-carboxaldehyde diethyl thioacetal of formula V where n is 2–3,

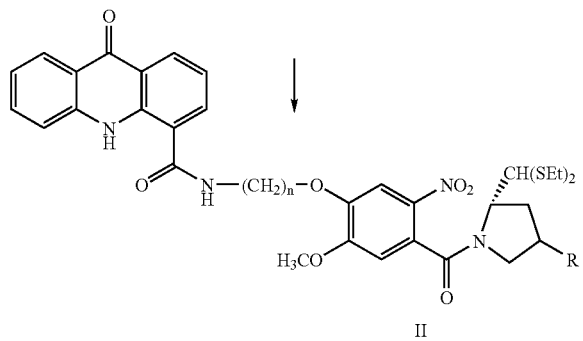

Formula II

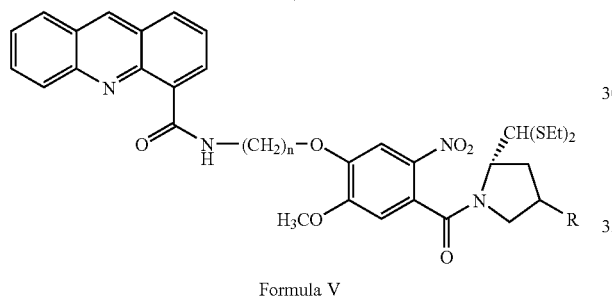

Formula V

The compound of formula II/formula V is isolated and then reduced with $SnCl_2.2H_2O$ in the presence of an organic solvent such as methanol up to a reflux temperature to obtain (2S)-N-{4-[n'-(4"-acridonylcarboxamido)-alkyl]-oxy-5-methoxy-2-aminobenzoyl}pyrrolidine-2-carboxaldehydediethylthioacetal of formula III/(2S)-N-{4-[n'-(4"-acridinyl-carboxamido)-alkyl]-oxy-5-methoxy-2-aminobenzoyl}pyrrolidine-2-carboxaldehyde diethyl thioacetal of formula VI were n is 2–3. The compounds of formula III/formula VI are then isolated by conventional methods.

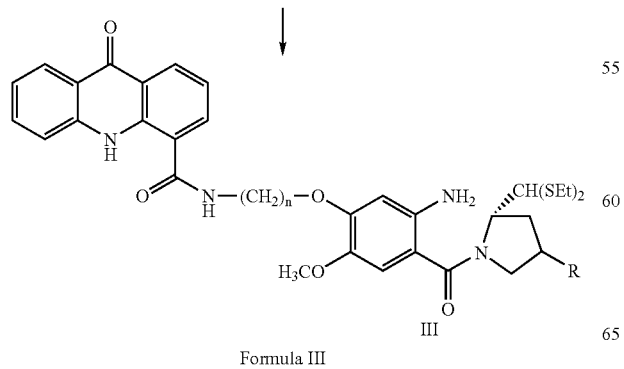

Formula III

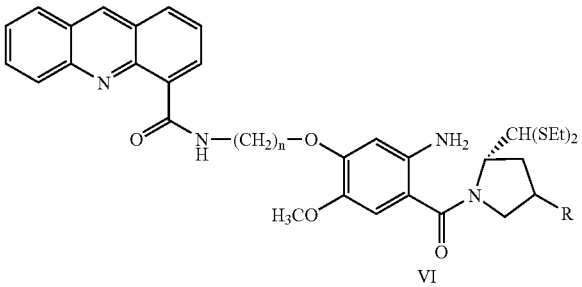

Formula VI

The compounds of formula III/formula VI with a known deprotecting agents in a conventional manner to give novel pyrrolo[2,1-c][1,4]benzodiazepine hybrids of formula IV/formula VII wherein n and R are as stated above

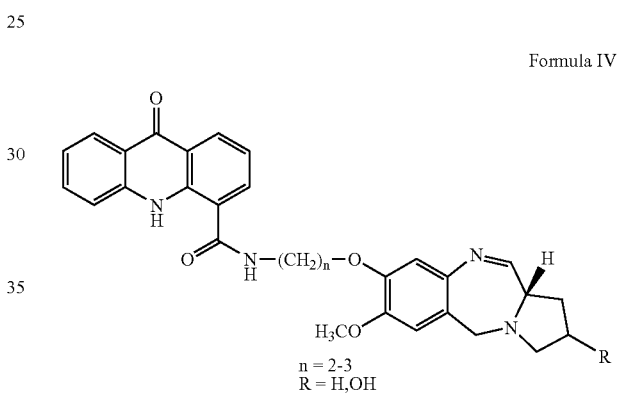

Formula IV

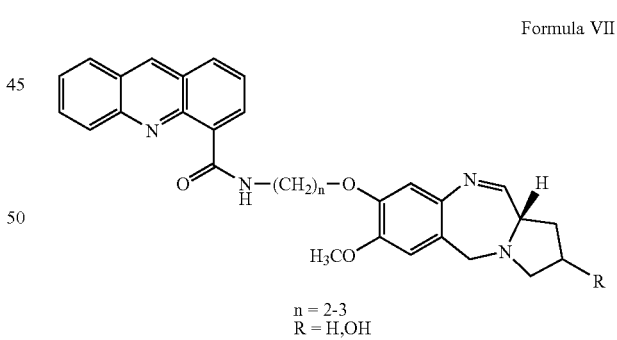

Formula VII

The organic solvent used for the reaction of the acridone/acridine acid with compound of formula I comprises dimethyl furan and the compound of formula II/formula V is isolated by washing with saturated $NaHCO_3$, brine, drying and evaporation of the solvent. The organic solvent used during the reduction of compound of formula II/formula V comprises methanol and the compound of formula III/formula V is isolated by adjusting the pH of the reaction mixture to about pH 8 with a saturated $NaHCO_3$ solution, diluting with ethyl acetate, filtering through celite and extracted an organic phase and drying the organic phase over $Na_2SO_4$.

The deprotecting agent used for obtaining the compound of formula IV/formula VII comprises $HgCl_2$ and $CaCO_3$ in MeCN-water (4:1).

The precursors, acridone acid (Atwell, G. J.; Cain, B. F.; Baguley, B. C.; Finlay, G. J.; Denny, W. A. *J. Med. Chem.* 1984, 27, 1481), acridine acid (Atwell G. J.; Rewcastle, G. W.; Baguley, B. C.; Denny, W. A. *J. Med. Chem.* 1987, 30, 664) and (2S)-N-[4-(n□-aminoalkyloxy)-5-methoxy-2-nitrobenzoyl]pyrrolidine-2-carboxaldehyde diethyl thioacetal of formula I (Thurston, D. E.; Morris, S. J.; Hartley, J. A. *Chem. Commun.* 1996, 563–565) have been prepared by literature methods.

Some representative compounds of formula IV/VII present invention are given below 1. 7-Methoxy-8-[2'-(4"-acridonylcarboxamido)ethyl]-oxy-(11aS)1,2,3,11a-tetra-hydro-5H-pyrrolo[2,1-c][1,4]benzodiazepin-5-one
2. 7-Methoxy-8-[2'-(4"-acridonylcarboxamido)ethyl]-oxy-(4R)-hydroxy-(11aS)1,2-3,11a-tetrahydro-5H-pyrrolo[2,1-c][1,4]benzodiazepin-5-one
3. 7-Methoxy-8-[3'-(4"-acridonylcarboxamido)propyl]-oxy-(11aS)1,2,3,11a-tetra-hydro-5H-pyrrolo[2,1-c][1,4]benzodiazepin-5-one
4. 7-Methoxy-8-[3'-(4"-acridonylcarboxamido)propyl]-oxy-(4R)-hydroxy-(11aS)1,2-3,11a tetrahydro-5H-pyrrolo[2,1-c][1,4]benzodiazepin-5-one
5. 7-Methoxy-8-[2'-(4"-acridinylcarboxamido)ethyl]-oxy-(11aS)-1,2,3,11a-tetrahydro-5H-pyrrolo[2,1-c][1,4]benzodiazepin-5-one
6. 7-Methoxy-8-[2'-(4"-acridinylcarboxamido)ethyl]-oxy-(4R)-hydroxy-(11aS)1,2,3-11a-tetrahydro-5-H-pyrrolo[2,1-c][1,4]benzodiazepin-5-one
7. 7-Methoxy-8-[3'-(4"-acridinylcarboxamido)propyl]-oxy-(11aS)1,2,3,11a-tetra-hydro-5H-pyrrolo[2,1-c][1,4]benzodiazepin-5-one
8. 7-Methoxy-8-[3'-(4"-acridinylcarboxamido)propyl]-oxy-(4R)-hydroxy-(11aS)1,2,-3,11a tetrahydro-5H-pyrrolo[2,1-c][1,4]benzodiazepin-5-one These new analogues of pyrrolo[2,1-c][1,4]benzodiazepine hybrids linked at C-8 position have shown promising DNA binding activity and efficient anticancer activity in various cell lines. The molecules synthesized are of immense biological significance with potential sequence selective DNA-binding property. This resulted in design and synthesis of new congeners as illustrated in Scheme-1/Scheme-2, which comprise:

1. The ether linkage at C-8 position of DC-81 intermediates with acridone/acridine ring moiety.
2. Up to refluxing the reaction mixture for 12–48 h.
3. Synthesis of C-8 linked PBD antitumour antibiotic hybrid imines.
4. Purification by column chromatography using different solvents like ethyl acetate, hexane, dichloromethane and methanol.

The reaction schemes are given below and are representative of the process of the invention.

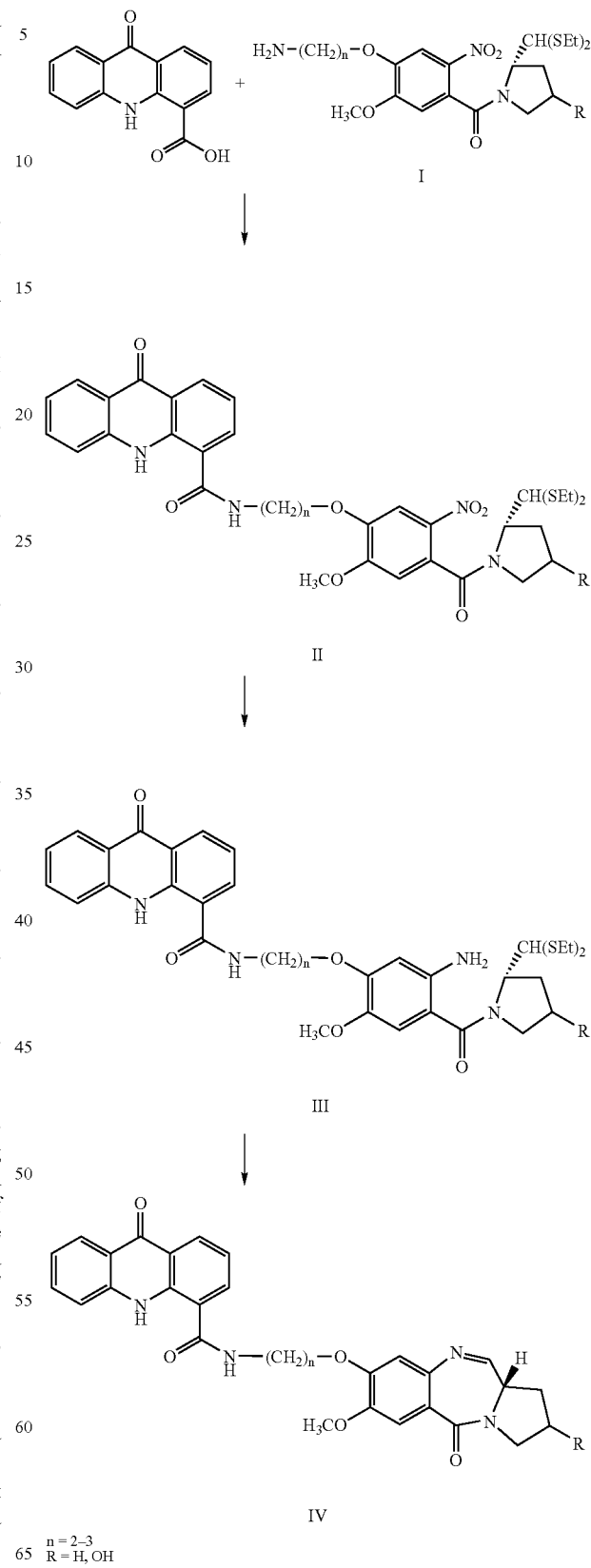

Scheme 2

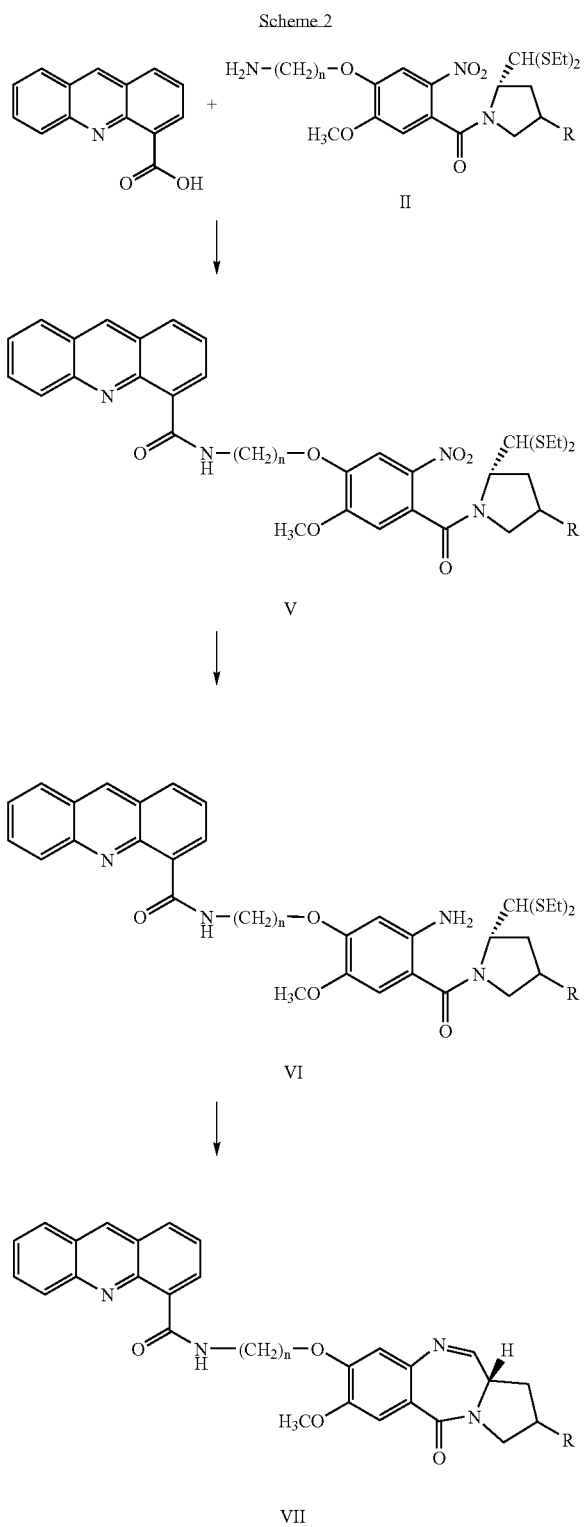

n = 2–3
R = H, OH

The following examples are given by way of illustration and therefore should not be construed to the present limit of the scope of invention.

EXAMPLE 1

Compound acridone acid (0.239 g, 1 mmol) was taken in dry DMF (10 mL), EDCI (0.203 g, 1.5 mmol) and HOBt (0.288 g, 1.5 mmol) was added and the mixture was cooled at 0–5° C. and the mixture was stirred for 30 min. A solution of (2S)-N-[4-(2□-aminoethyl)ox-5-methoxy-2-nitrobenzoyl]pyrrolidine-2-carboxaldehyde diethyl thioacetal of formula I (0.443 g, 1 mmol) in DMF was added to it at the same temperature and the solution was stirred at room temperature for overnight. The mixture was washed with saturated NaHCO$_3$ (50 mL), brine, dried and solvent was evaporated. The crude material was chromatographed over silicagel using ethylacetate/hexane (8.2) solvent to give compound (2S)-N-{4-[2'-(4"-acridonylcarboxamido)-ethyl]-oxy-5-methoxy-2-nitrobenzyl}pyrrolidine-2-carboxaldehyde diethyl thioacetal II as a yellow liquid.

The compound (2S)-N-{4-[2'-(4"-acridonylcarboxamido)-ethyl]-oxy-5-methoxy-2-nitro-benzoyl}pyrrolidine-2-carboxaldehyde diethyl thioacetal II (0.664 g, 1 mmol) was dissolved in methanol (15 mL) and added SnCl$_2$.2H$_2$O (1.128 g, 5 mmol) was refluxed for 2 h or until the TLC indicated that reaction was completed. The reaction mixture was then adjusted to pH 8 carefully with saturated NaHCO$_3$ solution, diluted with ethyl acetate, filtered through celite and extracted. The combined organic phase was dried over Na$_2$SO$_4$, and evaporated under vacuum to afford the crude compound (2S)-N-{4-[2'-(4"-acridonylcarboxamido)-ethyl]-oxy-5-methoxy-2-aminobenzoyl}pyrrolidine-2-carboxaldehyde diethyl thioacetal III.

A solution of compound (2S)-N-{4-[2'-(4"-acridonylcarboxamido)-ethyl]-oxy-5-methoxy-2-aminobenzoyl}pyrrolidine-2-carboxaldehyde diethyl thioacetal III (0.0634 g, 1 mmol), HgCl$_2$ (0.8145 g, 3 mmol) and CaCO$_3$ (0.3 g, 3 mmol) in MeCN-water (4:1) was stirred slowly at room temperature until TLC indicates complete loss of starting material. The reaction mixture was diluted with EtOAc (30 mL) and filtered through a celite bed. The clear yellow organic supernatant was extracted with saturated 5% NaHCO$_3$ (20 mL), brine (20 mL) and the combined organic phase is dried (Na$_2$SO$_4$). The organic layer was evaporated in vacuum and purified by column chromatography (90% CH$_2$Cl$_2$-MeOH) to give compound 7-methoxy-8-[2'-(4"-acridonylcarboxamido)ethyl]-oxy-(11aS)1,2,3,11a-tetrahydro-5H-pyrrolo[2,1-c][1,4]benzodiazepin-5-one.

EXAMPLE 2

Compound acridone acid (0.239 g, 1 mmol) was taken in dry DMF (10 mL), EDCI (0.203 g, 1.5 mmol) and HOBt (0.288 g, 1.5 mmol) was added and the mixture was cooled at 0–5° C. and the mixture was stirred for 30 min. A solution of (4R)-hydroxy-(2S)-N-[4-(2'-aminoethyl)-oxy-5-methoxy-2-nitrobenzoyl]pyrrolidine-2-carboxaldehyde diethylthioacetal of formula I (0.459 g, 1 mmol) in DMF was added to it at the same temperature and the solution was stirred at room temperature for overnight. The mixture was washed with saturated NaHCO$_3$ (50 mL), brine, dried and solvent was evaporated. The crude material was chromatographed over silica gel using ethyl acetate/hexane (8:2) solvent to give (4R)-hydroxy-( 2S)-N-{4-[2'-(4"-acridonylcarboxamido)-ethyl]-oxy-5-methoxy-2-nitrobenzoyl}pyrrolidine-2-carboxaldehyde diethyl thioacetal II as a yellow liquid.

The compound (4R)-hydroxy-(2S)-N-{4-[2'-(4"-acridonylcarboxamido)-ethyl]-oxy-5-methoxy-2-nitrobenzoyl}pyrrolidine-2-carboxaldehyde diethyl thioacetal II (0.680 g, 1 mmol) was dissolved in methanol (15 mL) and added SnCl$_2$.2H$_2$O (1.128 g, 5 mmol) was refluxed for 2 h or until the TLC indicated that reaction was completed. The reaction mixture was then adjusted to pH 8 carefully with saturated NaHCO$_3$ solution diluted with ethyl acetate, filtered through celite and extracted. The combined organic phase was dried over Na$_2$SO$_4$, and evaporated under vacuum to afford the crude compound (4R)-hydroxy-(2S)-N-{4-[2'-(4"-acridonylcarboxamido)-ethyl]-oxy-5-methoxy-2-aminobenzoyl}-pyrrol-idine-2-carboxaldehyde diethyl thioacetal III.

A solution of compound (4R)-hydroxy-(2S)-N-{4-[2'-(4"-acridonylcarboxamido)-ethyl]-oxy-5-methoxy-2-aminobenzoyl}pyrrolidine-2-carboxaldehyde diethyl thioacetal III (0.650 g, 1 mmol), HgCl$_2$ (0.8145 g, 3 mmol) and CaCO$_3$ (0.3 g, 3 mmol) in MeCN-water (4:1) was stirred slowly at room temperature until TLC indicates complete loss of starting material. The reaction mixture was diluted with EtOAc (30 mL) and filtered through a celite bed. The clear yellow organic supernatant was extracted with saturated 5% NaHCO$_3$ (20 ml), brine (20 mL) and the combined organic phase is dried (Na$_2$SO$_4$). The organic layer was evaporated in vacuum and purified by column chromatography (90% CH$_2$Cl$_2$-MeOH) to give compound 7-methoxy-8-[2'-(4"-acridonylcarboxamido)-ethyl]-oxy-(4R)-hydroxy-(11aS)1,2,3,-11a-tetrahydro-5H-pyrrolo[2,1-c][1,4]benzodiaze-pin-5-one.

EXAMPLE 3

Compound acridone acid (0.239 g, 1 mmol) was taken in dry DMF (10 mL), EDCI (0.203 g, 1.5 mmol) and HOBt (0.288 g, 1.5 mmol) was added and the mixture was cooled at 0–5° C. and the mixture was stirred for 30 min. A solution of (2S)-N-[4-(3'-aminopropyl)-oxy-5-methoxy-2-nitrobenzoyl]pyrrolidine-2-carboxaldehyde diethyl thioacetal of formula I (0.457 g, 1 mmol) in DMF was added to it at the same temperature and the solution was stirred at room temperature for overnight. The mixture was washed with saturated NaHCO$_3$ (50 mL), brine, dried and solvent was evaporated. The crude material was chromatographed over silica gel using ethylacetate/hexane (8:2) solvent to give compound (2S)-N-{4-[3'-(4"-acridonylcarboxamido)-propyl]-oxy-5-methoxy-2-nitro-benzoyl}pyrrolidine-2-carboxaldehyde diethyl thioacetal II as a yellow liquid.

$^1$H NMR (CDCl$_3$) δ 1.20–1.50 (m, 6H), 1.60–2.20 (m, 6H), 2.60–2.80 (m, 4H), 3.10–3.3 (m, 2H), 3.65–3.8 (m, 5H), 4.20–4.30 (m, 2H), 4.55–4.70 (m, 1H), 4.8 (d, 1H), 6.75 (s, 1H), 7.15 (t, 1H), 7.25 (t, 1H), 7.35 (d, 1H), 7.50 (s, 1H), 7.58–7.63 (t, 1H), 7.9 (bs, 1H), 8.15 (d, 1H), 8.35 (d, 1H), 8.55 (d, 1H); 12.3 (bs, 1H), MS (FAB) 679 [M+H]$^+$.

The compound (2S)-N-{4-[3'-(4"-acridonylcarboxamido)-propyl]-oxy-5-methoxy-2-nitrobenzoyl}pyrrolidine-2-carboxaldehyde diethyl thioacetal II (0.678 g, 1 mmol) was dissolved in methanol (15 mL) and added SnCl$_2$.2H$_2$O (1.128 g, 5 mmol) was refluxed for 2 h or until the TLC indicated that reaction was complete. The reaction mixture was then adjusted to pH 8 carefully with saturated NaHCO$_3$ solution, diluted with ethylacetate, filtered through celite and extracted. The combined organic phase was dried over Na$_2$SO$_4$, and evaporated under vacuum to afford crude (2S)-N-{4-[3'-(4"-acridonylcarboxamido)-propyl]-oxy-5-methoxy-2-aminobenzoyl}pyrrolidine-2-carboxaldehyde diethyl thioacetal III.

$^1$H NMR (CDCl$_3$) δ 1.20–1.45 (m, 6H), 1.55–2.35 (m, 6H), 2.60–2.85 (m, 6H), 3.6 (s, 3H), 3.7–3.8 (m, 2H), 4.15–4.25 (m 2H), 4.62–4.75 (m, 2H), 6.25 (s, 1H), 6.8 (s, 1H), 7.15–7.3 (m, 2H), 7.35 (d, 1H), 7.65–7.70 (t, 1H), 7.85 (br, 1H), 8.05 (d, 1H), 8.35 (d, 1H), 8.65 (d, 1H); 12.3 (bs, 1H).

A solution of compound (2S)-N-{4-[3'-(4"-acridonylcarboxamido)-propyl]-oxy-5-methoxy-2-aminobenzoyl}pyrrolidine-2-carboxaldehyde diethyl thioacetal III (0.648 g, 1 mmol), HgCl$_2$ (0.8145 g, 3 mmol) and CaCO$_3$ (0.3 g, 3 mmol) in MeCN-water (4:1) was stirred slowly at room temperature until TCL indicates complete loss of starting material. The reaction mixture was diluted with EtOAc (30 mL) and filtered through a celite bed. The clear yellow organic supernatant was extracted with saturated 5% NaHCO$_3$ (20 mL), brine (20 mL) and the combined organic phase is dried (Na$_2$SO$_4$). The organic layer was evaporated in vacuum and purified by column chromatography (90% CH$_2$Cl$_2$-MeOH) to give compound 7-methoxy-8-[3'-(4"-acridonylcarboxamido)propyl]-oxy-(11aS)1,2,3,11a-tetrahydro-5H-pyrrolo[2,1-c][1,4]-benzodiazepin-5-one.

$^1$H NMR (CDCl$_3$) δ 1.20–1.30 (m, 2H), 1.85–2.40 (m, 6H), 3.5–3.8 (m, 6H), 4.20–4.30 (m, 2H), 6.80 (s, 1H), 7.2–7.35 (m, 2H) 7.40 (d, 1H), 7.5 (s, 1H), 7.65 (d, 1H), 7.75 (t, 1H), 8.05 (d, 1H), 8.45 (d, 1H), 8.65 (d, 1H); 12.25 (bs, 1H), MS (FAB) 525 [M+H]$^+$.

EXAMPLE 4

Compound acridone acid (0.239 g, 1 mmol) was taken in dry DMF (10 mL), EDCI (0.203 g, 1.5 mmol) and HOBt (0.288 g, 1.5 mmol) was added and the mixture was cooled at 0–5° C. and the mixture was stirred for 30 min. A solution of (4R)-hydroxy-(2S)-N-[4-(3'-aminopropyl)-oxy-5-methoxy-2-nitrobenzoyl]pyrrolidine-2-carboxaldehyde diethyl thioacetal of formula I (0.473 g, 5 mmol) in DMF was added to it at the same temperature and the solution was stirred at room temperature for overnight. The mixture was washed with saturated NaHCO$_3$ (50 mL), brine, dried and solvent was evaporated. The crude material was chromatographed over silica gel using ethyl acetate/hexane (8:2) solvent to give (4R)-hydroxy-(2S)-N-{4-[3'-(4"-acridonylcarboxamido)-propyl]-oxy-5-methoxy-2-nitrobenzoyl}pyrrolidine-2-carboxaldehyde diethyl thioacetal II as a yellow liquid.

The compound (4R)-hydroxy-(2S)-N-{4-[3'-(4"-acridonylcarboxamido)-propyl]-oxy-5-methoxy-2-nitrobenzoyl}pyrrolidine-2-carboxaldehyde diethyl thioacetal II (0.694 g, 1 mmol) was dissolved in methanol (15 mL) and added SnCl$_2$.2H$_2$O (1.128 g, 5 mmol) was refluxed for 2 h or until the TLC indicated that reaction was completed. The reaction mixture was then adjusted to pH 8 carefully with saturated NaHCO$_3$ solution, diluted with ethyl acetate, filtered through celite and extracted. The combined organic phase was dried over Na$_2$SO$_4$, and evaporated under vacuum to afford the crude compound (4R)-hydroxy-(2S)-N-{4-[3'-(4"-acridonylcarboxamido)-propyl]-oxy-5-methoxy-2-aminobenzoyl}pyrro-lidine-2-carboxaldehyde diethyl thioacetal III.

A solution of compound (4R)-hyroxy-(2S)-N-{4-[3'-(4"-acridonylcarboxamido)-propyl]-oxy-5-methoxy-2-aminobenzoyl}pyrrolidine-2-carboxaldehyde diethyl thioacetal III (0.664 g, 1 mmol), HgCl$_2$ (0.8145 g, 3 mmol) and CaCO$_3$ (0.3 g, 3 mmol) in MeCN-water (4:1) was stirred slowly at room temperature until TLC indicates complete loss of starting material. The reaction mixture was diluted with EtOAc (30 mL) and filtered through a celite bed. The clear yellow organic supernatant was extracted with saturated 5% NaHCO$_3$ (20 mL), brine (20 mL) and the combined organic phase is dried (Na$_2$SO$_4$). The organic layer was evaporated in vacuum and purified by column chromatography (90% CH$_2$Cl$_2$-MeOH) to give compound 7-methoxy-8-[3'-(4"-acridonylcarboxamido) propyl]-oxy-(4R)-hydroxy-(11aS) 1,2,3,11a-tetrahydro-5H-pyrrolo[2,1-c][1,4]benzodiaze pin-5-one.

EXAMPLE 5

Compound acridine acid (0.223 g, 1 mmol) was taken in dry DMF (10 mL), EDCI (0.203 g, 1.5 mmol) and HOBt (0.288 g, 1.5 mmol) was added and the mixture was cooled at 0–5° C. and the mixture was stirred for 30 min. A solution of (2S)-N-[4-(2'-aminoethyl)-oxy-5-methoxy-2-nitrobenzoyl]pyrrolidine-2-carboxaldehyde diethyl thioacetal of formula I (0.443 g, 1 mmol) in DMF was added to it at the same temperature and the solution was stirred at room temperature for overnight. The mixture was washed with saturated NaHCO$_3$ (50 mL), brine, dried and solvent was evaporated. The crude material was chromatographed over silica gel using ethyl acetate/hexane (8:2) solvent to give compound (2S)-N-{4-[2'-(4"-acridinylcarboxamido)-ethyl]-oxy-5-methoxy-2-nitrobenzo-yl}pyrrolidine-2-carboxaldehyde diethyl thioacetal II as a yellow liquid.

The compound (2S)-N-{4-[2'-(4"-acridinylcarboxamido)-ethyl]-oxy-5-methoxy-2-nitrobenzoyl}-pyrrolidine-2-carboxaldehyde diethyl thioacetal II (0.648 g, 1 mmol) was dissolved in methanol (15 mL) and added SnCl$_2$.2H$_2$O (1.128 g, 5 mmol) was refluxed for 2 h or until the TLC indicated that reaction was completed. The reaction mixture was then through celite and extracted. The combined organic phase was dried over Na$_2$SO$_4$, and evaporated under vacuum to afford the crude compound (2S)-N-{4-[2'-(4"-acridinylcarboxamido)-ethyl]-oxy-5-methoxy-2-aminobenzoyl)pyrrolidine-2-carboxaldehyde diethyl thioacetal III.

A solution of compound (2S)-N-{4-[2'-(4"-acridinylcarboxamido)-ethyl]-oxy-5-methoxy-2-aminobenzoyl)pyrrolidine-2-carboxaldehyde diethyl thioacetal III (0.618 g, 1 mmol), HgCl$_2$ (0.8145 g, 3 mmol) and CaCO$_3$ (0.3 g, 3 mmol) in MeCN-water (4:1) was stirred slowly at room temperature until TLC indicates complete loss of starting material. The reaction mixture was diluted with EtOAc (30 mL) and filtered through a celite bed. The clear yellow organic supernatant was extracted with saturated 5% NaHCO$_3$ (20 mL), brine (20 mL) and the combined organic phase is dried (Na$_2$SO$_4$). The organic layer was evaporated in vacuum and purified by column chromatography (90% CH$_2$Cl$_2$-MeOH) to give compound 7-methoxy-8-[2'-(4"-acridinylcarboxamido)ethyl]-oxy-(11aS)1,2,3,11a-tetrahydro-5H-pyrrolo[2,1-c][1,4]benzodiazepin-5-one.

EXAMPLE 6

Compound acridine acid (0.223 g, 1 mmol) was taken in dry DMF (10 mL), EDCI (0.203 g, 1.5 mmol) and HOBt (0.288 g, 1.5 mmol) was added and the mixture was cooled at 0–5° C. and the mixture was stirred for 30 min. A solution of (4R)-hydroxy-(2S)-N-[4-(2'-aminoethyl)-oxy-5-methoxy-2-nitrobenzoyl]pyrrolidine-2-carboxyldehyde diethyl thioacetal for formula I (0.459 g, 1 mmol) in DMF was added to it at the same temperature and the solution was stirred at room temperature for overnight. The mixture was washed with saturated NaHCO$_3$ (50 mL), brine, dried and solvent was evaporated. The crude material was chromatographed over silica gel using ethyl acetate/hexane (8:2) solvent to give (4R)-hydroxy-(2S)-N-{4-[2'-(4"-acridinyl-carboxamido)-ethyl-oxy-5-methoxy-2-nitrobenzoyl}pyrrolidine-2-carboxaldehyde diethyl thioacetal II as a yellow liquid.

The compound (4R)-hydroxy-(2S)-N-{4-[2'-(4"-acridinylcarboxamido)-ethyl]-oxy-5-methoxy-2-nitrobenzoyl}pyrrolidine-2-carboxaldehyde diethyl thioacetal II (0.664 g, 1 mmol) was dissolved in methanol (15 mL) and added SnCl$_2$.2H$_2$O (1.128 g, 5 mmol) was refluxed for 2 h or until the TLC indicated that reaction was completed. The reaction mixture was then adjusted to pH 8 carefully with saturated NaHCO$_3$ solution, diluted with ethyl acetate, filtered through celite and extracted. The combined organic phase was dried over Na$_2$SO$_4$, and evaporated under vacuum to afford the crude compound (4R)-hydroxy-(2S)-N-{4-[2'-(4"-acridinylcarboxamido)-ethyl]-oxy-5-methoxy-2-aminobenzoyl}pyrro-lidine-2-carboxaldehyde diethyl thioacetal III.

A solution of compound (4R)-hydroxy-(2S)-N-{4-[2'-(4"-acridinylcarboxamido)-ethyl]-oxy-5-methoxy-2-aminobenzoyl}pyrrolidine-2-carboxaldehyde diethyl thioacetal III (0.634 g, 1 mmol), HgCl$_2$ (0.8145 g, 3 mmol) and CaCO$_3$ (0.3 g, 3 mmol) in MeCN-water (4:1) was stirred slowly at room temperature until TLC indicates complete loss of starting material. The reaction mixture was diluted with EtOAc (30 mL) and filtered through a celite bed. The clear yellow organic supernatant was extracted with saturated 5% NaHCO$_3$ (20 mL), brine (20 mL) and the combined organic phase is dried (Na$_2$SO$_4$). The organic layer was evaporated in vacuum and purified by column chromatography (90% CH$_2$Cl$_2$-MeOH) to give compound 7-methoxy-8-[2'-(4"-acridinylcarboxamido)-ethyl]-oxy-(4R)-hyroxy-(11aS)1,2,3-11a-tetrahydro-5H-pyrrolo[2,1-c][1,4]benzodiaze-pin-5-one.

EXAMPLE 7

Compound acridine acid (0.223 g, 1 mmol) was taken in dry DMF (10 mL), EDCI (0.203 g, 1.5 mmol) and HOBt (0.288 g, 1.5 mmol) was added and the mixture was cooled at 0–5° C. and the mixture was stirred for 30 min. A solution of (2S)-N-[4-(3'-amino-propyl]oxy-5-methoxy-2-nitrobenzoyl]pyrrolidine-2-carboxaldehyde diethyl thioacetal of formula I (0.457 g, 1 mmol) in DMF was added to it at same temperature and the solution was stirred at room temperature for overnight. The mixture was washed with saturated NaHCO$_3$ (50 mL), brine, dried and solvent was evaporated. The crude material was chromatographed over silica gel using ethylacetate/hexane (8:2) solvent to give (2S)-N-{4-[2'-(4"-acridinylcarboxamido)-propyl]-oxy-5-methoxy-2-nitroben-zoyl}pyrrolidine-2-carboxaldehyde diethyl thioacetal II as a yellow liquid.

$^1$H NMR (CDCl$_3$) δ 1.20–1.50 (m, 6H), 1.60–2.40 (m, 6H), 2.60–2.85 (m, 4H), 3.10–3.25 (m, 2H), 3.85–3.9 (m, 5H), 4.20–4.30 (m, 2H), 4.65–4.70 (m, 1H), 4.82 (d, 1H), 6.8(s, 1H), 7.4–7.8 (m, 4H), 7.85–8.05 (t, 2H), 8.10 (d, 1H), 8.82 (s, 1H), 11.9(bs, 1H), MS (FAB) 663 [M+H]$^+$.

The compound (2S)-N-{4-[3'-(4"-acridinylcarboxamido)-propyl]-oxy-5-methoxy-2-nitrobenzoyl}pyrrolidine-2-carboxaldehyde diethyl thioacetal II (0.662 g, 1 mmol) was dissolved in methanol (15 mL) and added SnCl$_2$.2H$_2$O (1.128 g, 5 mmol) was refluxed for 2 h or until the TLC indicated that reaction was completed. The reaction mixture was then adjusted to pH 8 carefully with saturated NaHCO$_3$ solution, diluted with ethyl acetate, filtered through celite and extracted. The combined organic phase was dried over Na$_2$SO$_4$, and evaporated under vacuum to afford the crude compound (2S)-N-{4-[3'-(4"-acridinylcarboxamido)-propyl]-oxy-5-methoxy-2-aminobenzoyl}pyrrolidine-2-carboxaldehyde diethyl thioacetal III.

¹H NMR (CDCl₃) δ 1.20–1.5 (m, 6H), 1.60–2.40 (m, 6H), 2.60–2.80 (m, 4H), 3.55–3.7 (m, 2H), 3.8 (s, 3H), 3.9–4.00 (m, 2H), 4.15–4.25 (m, 2H), 4.65–4.80 (m 2H), 6.25 (s, 1H), 6.8 (s, 1H), 7.50–7.80 (m, 4H), 7.90–8.00 (m, 2H), 8.85 (s, 1H), 8.95 (d, 1H), 11.9 (bs, 1H).

A solution of compound (2S)-N-{4-[3-(4"-acridinylcarboxamido)-propyl]-oxy-5-methoxy-2-aminobenzoyl}pyrrolidine-2-carboxaldehyde diethyl thioacetal III (0.632 g, 1 mmol), HgCl₂ (0.8145 g, 3 mmol) and CaCO₃ (0.3 g, 3 mmol) in MeCN-water (4:1) was stirred slowly at room temperature until TLC indicates complete loss of starting material. The reaction mixture was diluted with EtOAc (30 mL) and filtered through acelite bed. The clear yellow organic supernatant was extracted with saturated 5% NaHCO₃ (20 mL),brine (20 mL) and the combined organic phase is dried (Na₂SO₄). The organic layer was evaporated in vacuum and purified by column chromatography (90% CH₂Cl₂-MeOH) to give compound 7-methoxy-8-[3'-(4"-acridinylcarboxamido)propyl]-oxy-(11aS)1,2,3,11a-tetrahydro-5H-pyrrolo [2,1-c][1,4]benzodiazepin-5-one.

¹H NMR (CDCl₃) δ 1.20–1.30 (m, 2H), 1.95–2.45 (m, 6H), 3.5–3.8 (m, 5H), 4.25–4.45 (m, 3H), 6.80 (s, 1H), 7.50–7.80 (m, 5H), 7.95–8.1 (m, 2H), 8.15 (d, 1H), 8.90 (s, 1H), 9.00 (d, 1H); 12.00 (bs, 1H), MS (FAB) 509 [M+H]⁺.

EXAMPLE 8

Compound acridine acid (0.223 g, 1 mmol) was taken in dry DMF (10 mL), (0.203 g, 1.5 mmol) and HOBt (0.288 g, 1.5 mmol) was added and the mixture was cooled at 0–5° C. and the mixture was stirred for 30 min. A solution of (4R)-hydroxy-(2S)-N-[4-(3'-aminopropyl)-oxy-5-methoxy-2-nitrobenzoyl]pyrrolidine-2-carboxaldehyde diethyl thioacetal of formula I(0.473 g, 5 mmol) in DMF was added to it at the same temperature and the solution was stirred at room temperature for overnight. The mixture was washed with saturated NaHCO₃ (50 mL), brine, dried and solvent was evaporated. The crude material was chromatographed over silica gel using ethyl acetate/hexane (8:2) solvent to give compound (4R)-hydroxy-(2S)-N-}4-[3'-(4"-acridinyl-carboxamido)-propyl]-oxy-5-methoxy-2-nitrobenzoyl}pyrrolidine-2-carboxaldehyde diethyl thioacetal II as a yellow liquid.

The compound (4R)-hydroxy-(2S)-N-{4-[3'-(4"-acridinylcarboxamido)-propyl]-oxy-5-methoxy-2-nitrobenzoyl}pyrrolidine-2-carboxaldehyde diethyl thioacetal II (0.678 g, 1 mmol) was dissolved in methanol (15 mL) and added SnCl₂.2H₂O (1.128 g, 5 mmol) was refluxed for 2 h or until the TLC indicated that reaction was completed. The reaction mixture was then adjusted to pH 8 carefully with saturated NaHCO₃ solution, diluted with ethyl acetate, filtered through celite and extracted. The combined organic phase was dried over Na₂SO₄, and evaporated under vacuum to afford the crude compound (4R)-hydroxy-(2S)-N-{4-[3'-(4"-acridinylcarboxamido)-propyl]-oxy-5-methoxy-2-aminobenzoyl}pyrro-lidine-2-carboxaldehyde diethyl thioacetal III.

A solution of compound (4R)-hydroxy-(2S)-N-{4-[3'-(4"-acridinylcarboxamido)-pyropyl]-oxo-5-methoxy-2-aminobenzoyl}pyrrolidine-2-carboxaldehyde diethyl thioacetal III (0.648 g, 1 mmol), HgCl₂ (0.8145 g, 3 mmol) and CaCO₃ (0.3 g, 3 mmol) in MeCN-water (4:1) was stirred slowly at room temperature until TLC indicates complete loss of starting material. The reaction mixture was diluted with EtOAc (30 mL) and filtered through a celite bed. The clear yellow organic supernatant was extracted with saturated 5% NaHCO₃ (20 mL), brine (20 mL) and the combined organic phase is dried (Na₂SO₄). The organic layer was evaporated in vacuum and purified by column chromatography (90% CH₂Cl₂-MeOH) to give compound 7-methoxy-8-[3'-(4"-acridinyl carboxamido) propyl]-oxy-(4R)-hydroxy-(11aS) 1,2,3,11a-tetrahydro-5H-pyrrolo[2,1-c]-[1,4]-benzodia-zepin-5-one.

Biological Activity: In vitro biological activity studies were carried out at National Cancer Institute (USA).

Cytotoxicity: 7-methoxy-8-[3'-(4"-acridonylcarboxamido)propyl]-oxy-(11aS)1,2,3,11a-tetrahydro-5H-pyrrolo [2,1-c][1,4]benzodiazepin-5-one of formula IV was evaluated for primary anti-cancer activity (Table 1) and in vitro against sixty human tumour cells derived from nine cancer types (leukemia, non-small-cell lung, colon, CNS, melanoma, ovarian, prostate, and breast cancer). For each compound, dose response curves for each cell line were measured at a minimum of five concentrations at 10 fold dilutions. A protocol of 48 h continuous drug expose was used and a sulforhodamine B (SRB) protein assay was used to estimate cell viability or growth. The concentration causing 50% cell growth inhibition (GI50), total cell growth inhibition (TGI, 0% growth) and 50% cell death (LC50, −50% growth) compared with the control was calculated. The mean graph midpoint value s of $\log_{10}$TGI and log10LC50 as well as $\log_{10}$ GI50 for IV are listed in Table 2. The mean graph itself is shown in Table 4. As demonstrated by mean graph pattern, compound IV exhibits an interesting profile of activity and selectivity for various cell lines. The mean graph mid point of $\log_{10}$ TGI and $\log_{10}$ LC50 showed similar pattern to the $\log_{10}$ GI50 mean graph mid points.

TABLE 1

In vitro one dose primary anticancer assay[a] acridone linked PBD hybrid of IV

| | Growth percentages | | |
|---|---|---|---|
| PBD hybrid | (Lung) NCI-H460 | (Breast) MCF7 | (CNS) SF-268 |
| IV | 0 | 0 | 10 |

[a]One dose of IV at 10⁻⁴ molar concentration

The novel pyrrolobenzodiazepine hybrid 7-methoxy-8-[3'-(4"-acridonylcarboxamido)-propyl]-oxy-(11aS)1,2,3,11a-tetrahydro-5H-pyrrolo[2,1-c][1,4]benzodiazepin-5-one of formula IV has shown to posses <10 nano molar potency (at the $LC_{50}$ level) against one melanoma cancer (UACC-62) and 0.1 micro molar potency against colon cancer (HCC-2998), CNS cancer (SNB-75), breast cancer (MDA-MB-435) and also have >10 micro molar potency against two melanoma cancer cell lines (LOXIMVI, M14) and one renal cancer (SN12C). The $LC_{50}$ values of nine cancers (average of six to nine cancer cell lines) of compound 7-methoxy-8-[3'-(4"-acidonylcarboxamido)-propyl]-oxy-(11aS)1,2,3,11a-tetrahydro-5H-pyrrolo[2,1-c][1,4]benzodiazepin-5-one of formula IV listed in Table 3.

TABLE 2 log₁₀ GI50 log₁₀ TGI and log₁₀ LC50 mean graphs midpoints(MG_MID) of in vitro cytotoxicity data for the compound IV against human tumour cell lines.

| Compound | Log₁₀ GI50 | Log₁₀ TGI | Log₁₀ LC50 |
|---|---|---|---|
| IV | −7.73 | −5.56 | −4.32 |

TABLE 3

Log LC50 (concentration in mol/L causing 50% lethality) Values for Compounds IV

| Cancer | Compound IV |
|---|---|
| Leukemia | −4.00 |
| non-small-cell lung | −4.14 |
| Colon | −4.33 |
| CNS | −4.425 |
| Melanoma | −5.09 |
| Ovarian | −4.012 |
| Renal | −4.27 |
| Prostate | −4.00 |
| Breast | −4.40 |

Each cancer type represents the average of six to nine different cancer cell lines.

What is claimed is:

1. A compound of the formula given below wherein R is H or OH and n is 2 or 3

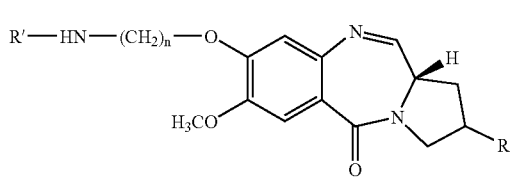

where R' is

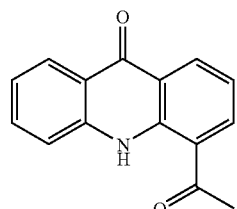

or

2. A compound as claimed in claim 1 of the structure

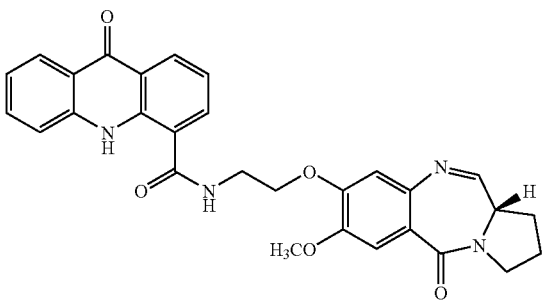

3. A compound as claimed in claim of the structure

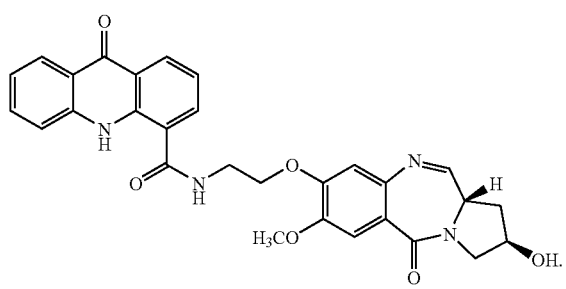

4. A compound as claimed in claim 1 of the structure

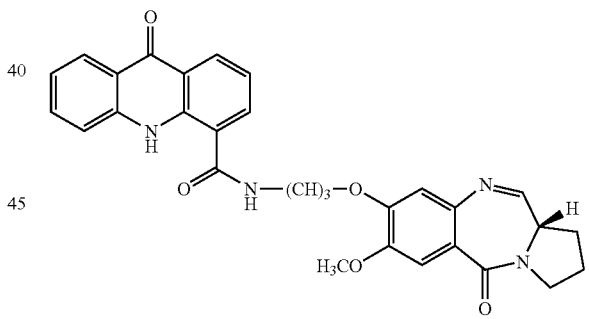

5. A compound as claimed in claim 1 of the structure

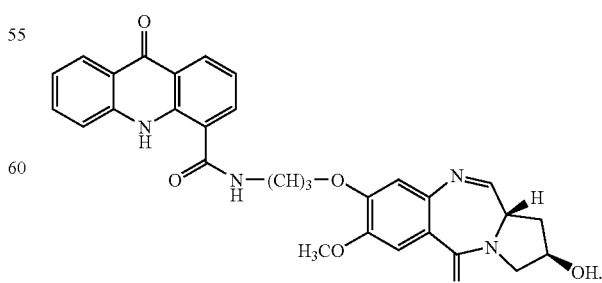

6. A compound as claimed in claim 1 of the structure

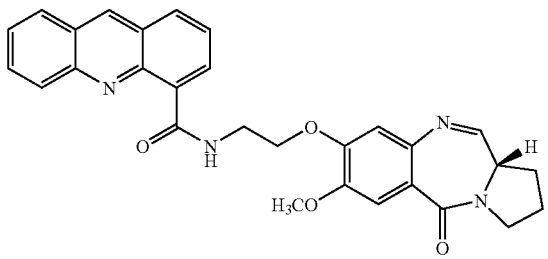

7. A compound as claimed in claim 1 of the structure

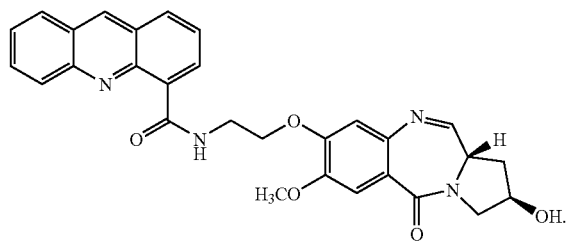

8. A compound as claimed in claim 1 of the structure

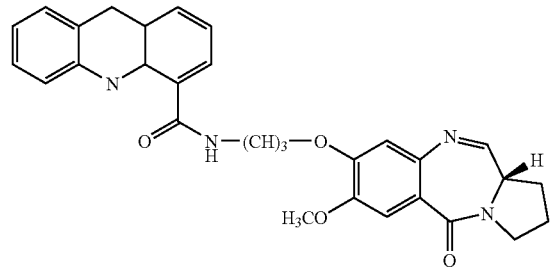

9. A compound as claimed in claim 1 of the structure

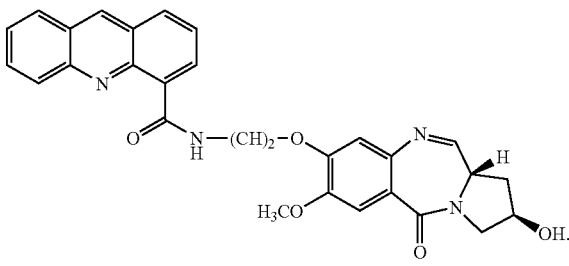

10. A process for the preparation of a compound of the formula wherein R is H or OH and n is 2 or 3

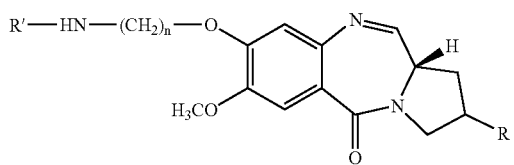

-continued where R' is 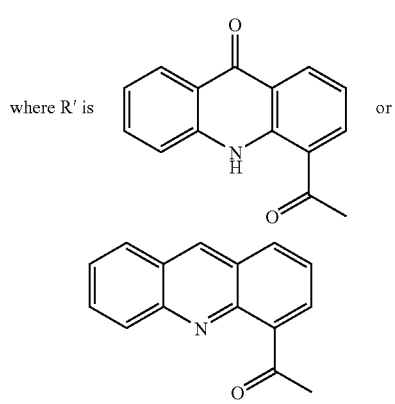 or

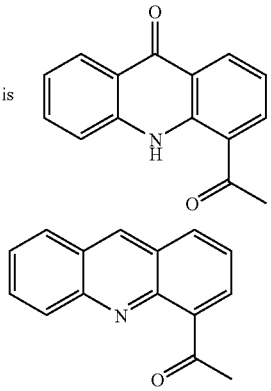

the process comprising the steps of:
a) reacting an acridone or an acridine acid with (2S)-N-[4-(n'-aminoalkyloxy)-5-methoxy-2-nitrobenzoyl]-pyrrolidine-2-carboxaldehyde diethyl thioacetal of formula I

FORMULA I

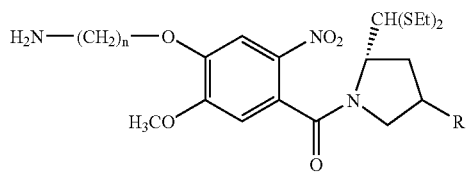

in the presence of EDCI and HOBt in organic solvent for a period of 24 h to obtain (2S)-N-{4-[n'-(4"-acrido-nylcarboxamido)-alkyl]-oxy-5-methoxy-2-nitrobenzoyl}pyrrolidine-2-carboxaldehyde diethyl thioacetal of formula II/(2S)-N-{4-[n'-(4"-acridinylcarboxamido)-alkyl]-oxy-5-methoxy-2-nitrobenzoyl}pyrrolidine-2-carboxaldehyde diethyl thioacetal of formula V where n is 2 or 3 and R is H or OH;

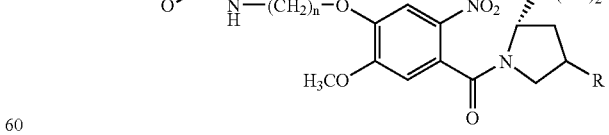

FORMULA II

-continued

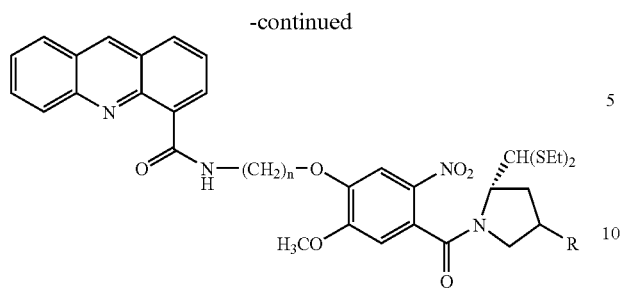

FORMULA V b) isolating the compound of formula II/formula V, and
c) then reducing the compounds of formula II/formula V with SnCl$_2$.2H$_2$O in presence of an organic solvent up to a reflux temperature;
d) isolating the (2S)-N-{4-[n'-(4"-acridonylcarboxa-mido)-alkyl]-oxy-5-methoxy-2-aminobenzoyl}pyrrolidine-2-carboxaldehydediethylthioacetal of formula III/ (2S*)-N-{4-[n'-(4"-acridinylcarboxy-amido)-alkyl]-oxy-5-methoxy-2-aminobenzoyl}pyrrolidine-2-carboxaldehyde diethyl thioacetal of formula VI where n is 2 or 3 and R is H or OH;

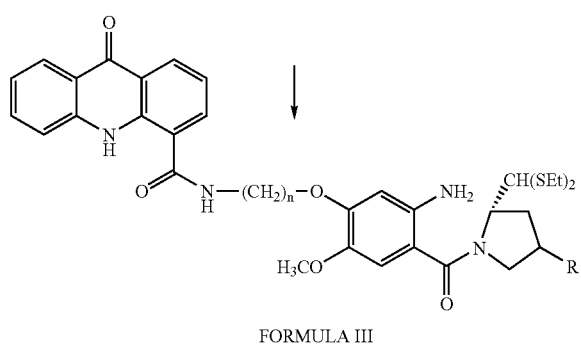

FORMULA III

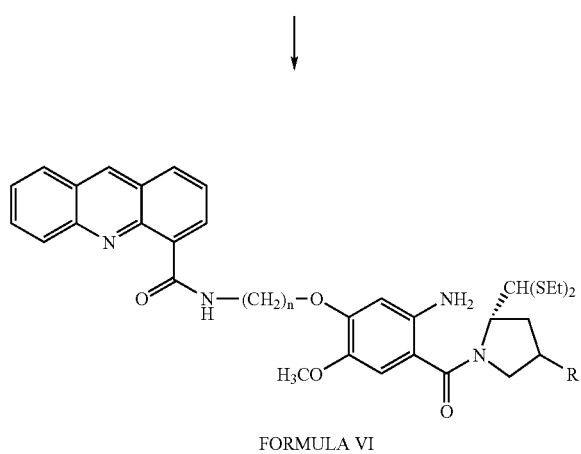

FORMULA VI and
e) reacting the compound of formula III/formula VI with a deprotecting agent to obtain the compound of formula

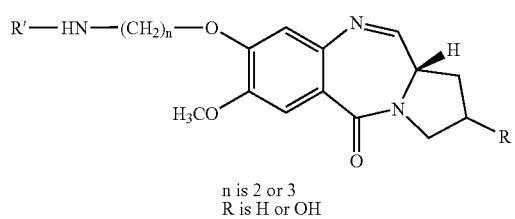

n is 2 or 3
R is H or OH where R' = 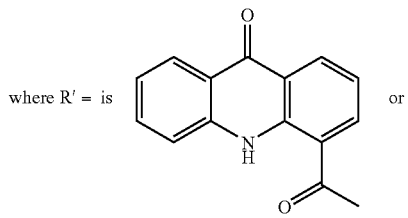 or

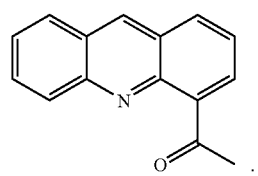

11. The process as claimed in claim 10 wherein the organic solvent used for the reaction of the acridone/acridine acid with the compound of formula I comprises dimethyl furan.
12. The process as claimed in claim 10 wherein the compound of formula II/formula V is isolated by washing with saturated NaHCO$_3$, brine, drying and evaporating the solvent.
13. The process as claimed in claim 10 wherein the organic solvent used during the reduction of compound of formula II/formula V comprises methanol.
14. The process as claimed in claim 10 wherein the compound of formula III/formula V is isolated by adjusting the pH of the reaction mixture to about pH 8 with a saturated NaHCO$_3$ solution, diluting with ethyl acetate, filtering through celite and extracting an organic phase and drying the organic phase over Na$_2$SO$_4$.
15. The process as claimed in claim 10 wherein the deprotecting agent used for obtaining the compound of formula IV/formula VII comprises HgCl$_2$ and CaCO$_3$ in MeCH-water (4:1).
16. The pharmaceutical composition comprising a pharmaceutically effective amount of a compound of the formula given below wherein R is H or OH and n is 2 or 3 and a pharmaceutically acceptable additive.

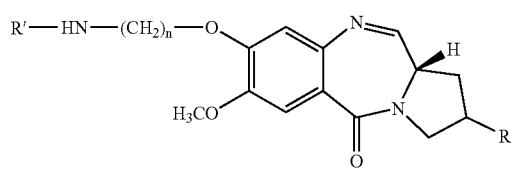

-continued where R' is 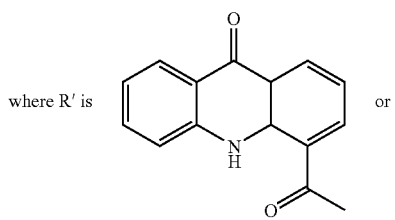 or

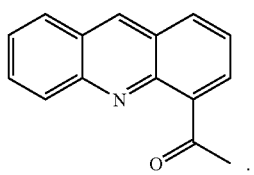

17. A method for the treatment of cancer wherein the cancer is selected from the group consisting of leukemia, non-small cell, lung, colon, CNS, melanoma ovarian, renal, prostate and breast in a mammal suffering from the same comprising administering a pharmaceutically effective amount of a compound of the formula

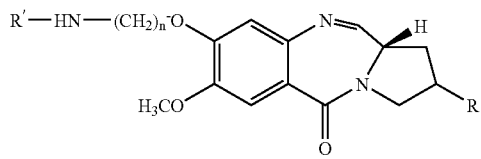

where R' is 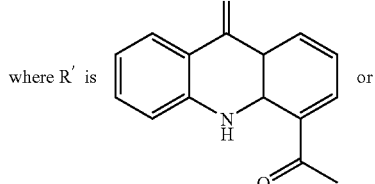 or

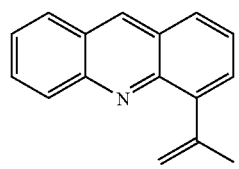

wherein R is H or OH and n is 2–3 to the mammal.

18. A method as claimed in claim 17 wherein the mammal is a human being.

* * * * *